(12) United States Patent
Chu

(10) Patent No.: US 11,002,671 B1
(45) Date of Patent: May 11, 2021

(54) SYSTEMS AND METHODS FOR MAPPING ABSORPTION SPECTROSCOPY SCANS AND VIDEO FRAMES

(71) Applicant: Soter Technologies, LLC, Ronkonkoma, NY (US)

(72) Inventor: Cary Chu, Mount Sinai, NY (US)

(73) Assignee: SOTER TECHNOLOGIES, LLC, Ronkonkoma, NY (US)

( * ) Notice: Subject to any disclaimer, the term of this patent is extended or adjusted under 35 U.S.C. 154(b) by 0 days.

(21) Appl. No.: 16/886,121

(22) Filed: May 28, 2020

(51) Int. Cl.
*G01N 21/3563* (2014.01)
*H04N 7/18* (2006.01)
(Continued)

(52) U.S. Cl.
CPC ....... *G01N 21/3563* (2013.01); *G01N 33/227* (2013.01); *G06K 9/00771* (2013.01);
(Continued)

(58) Field of Classification Search
CPC ........... G01N 21/31; G01N 2021/1793; G01N 2021/3137; G01N 21/255; G01N 21/3103; G01N 2021/3107; G01N 2021/3125; G01N 2021/3122; G01N 2021/3118; G01N 2021/3129; G01N 2021/3133; G01N 21/314; G01N 2021/3148; G01N 21/3151; G01N 2021/3155; G01J 2003/2826; G01J 3/2803; G01J 3/36
(Continued)

(56) References Cited

U.S. PATENT DOCUMENTS 6,998,991 B1   2/2006 Goldstein et al.
8,175,297 B1   5/2012 Ho et al.
(Continued)

FOREIGN PATENT DOCUMENTS

CA   2740454 C   11/2015
KR   101778681 B1   9/2017

OTHER PUBLICATIONS

International Preliminary Report on Patentability dated Feb. 18, 2020 by the U.S. Patent and Trademark Office, acting as International Searching Authority, in corresponding International Application No. PCT/US2018/000223.
(Continued)

*Primary Examiner* — Nathnael Aynalem
(74) *Attorney, Agent, or Firm* — Carter, Deluca & Farrell LLP; George Likourezos

(57) ABSTRACT

A method of detecting a substance includes, for each position of a plurality of positions in a field of view of an environment: emitting from a light source a light beam including a predetermined wavelength that is absorbable by a constituent of the substance, controlling at least one mirror to direct the emitted light beam to the position in the field of view, detecting by a detector light resulting from the emitted light beam, and determining whether the constituent of the substance is present at the position in the field of view based on characteristics of the detected light; generating a detection map indicating a presence or an absence of the substance at the plurality of positions in the field of view of the environment; capturing, by an image capture device, an image of the environment; and identifying a portion of the captured image having the substance based on the detection map.

20 Claims, 7 Drawing Sheets

(51) Int. Cl.
*H04N 5/225* (2006.01)
*G01N 33/22* (2006.01)
*G06K 9/00* (2006.01)

(52) U.S. Cl.
CPC ............. *H04N 5/2256* (2013.01); *H04N 7/18* (2013.01); *G01N 2201/0612* (2013.01); *G01N 2201/0636* (2013.01)

(58) Field of Classification Search
USPC ................. 250/390.04; 702/28; 348/146
See application file for complete search history.

(56) References Cited

U.S. PATENT DOCUMENTS

| | | | | |
|---|---|---|---|---|
| 2002/0031843 A1* | 3/2002 | Harmon | ............... | G01N 21/31 436/518 |
| 2002/0171042 A1* | 11/2002 | Chen | ............... | G01T 1/2928 250/390.04 |
| 2005/0207943 A1* | 9/2005 | Puzey | ............... | C12Q 1/04 422/82.05 |
| 2010/0127865 A1 | 5/2010 | Marriam et al. | | |
| 2011/0221889 A1* | 9/2011 | Knox | ............... | G08B 17/107 348/135 |
| 2014/0207285 A1* | 7/2014 | Sakabe | ............... | B25J 9/1676 700/259 |
| 2015/0051498 A1* | 2/2015 | Darty | ............... | G16H 50/50 600/477 |
| 2015/0181137 A1* | 6/2015 | Terashima | ............... | G01N 21/3151 348/162 |
| 2015/0323427 A1 | 11/2015 | Sharp | | |
| 2016/0069743 A1* | 3/2016 | McQuilkin | ............... | A22B 5/007 356/416 |
| 2016/0163168 A1 | 6/2016 | Brav et al. | | |
| 2016/0212828 A1 | 7/2016 | Leinen et al. | | |
| 2018/0284240 A1* | 10/2018 | LaChapelle | ............... | G01S 17/10 |

OTHER PUBLICATIONS

International Search Report and Written Opinion for Application No. PCT/US18/00223 dated Nov. 15, 2018.

* cited by examiner

SYSTEMS AND METHODS FOR MAPPING ABSORPTION SPECTROSCOPY SCANS AND VIDEO FRAMES

FIELD

The present technology relates generally to systems and methods for residue scanning and, more particularly, for mapping residue scanning to video frames.

BACKGROUND

Substance detectors and video cameras are both beneficial for various reasons. Substance detectors, such as vape or smoke detectors, can identify harmful activities or situations and provide an alert when there is a detection. While substance detectors are beneficial for detection, they do not identify the source of the harmful activity or situation. Video cameras can be used for surveillance and for identification. However, video cameras do not detect harmful activities or situations. Accordingly, there is interest in developing improved detection and surveillance systems.

SUMMARY

The present disclosure relates to systems and methods for residue scanning and for mapping residue scanning to video frames.

In accordance with aspects of the present disclosure, a detection system includes a light source configured to emit a light beam where the light beam includes a predetermined wavelength that is absorbable by a constituent of a substance; a detector configured to detect light resulting from the emitted light beam; at least one mirror including a drive motor; an image capturing device configured to capture an image of an environment; and a controller in communication with the light source, the at least one mirror, and the detector, where the controller is configured to, for each position of a plurality of positions in a field of view of the environment: control the light source to emit the light beam, control the at least one mirror to direct the emitted light beam to the position in the field of view, control the detector to detect light resulting from the emitted light beam, and determine whether the constituent of the substance is present at the position in the field of view based on characteristics of the detected light, wherein the controller is further configured to generate a detection map indicating a presence or an absence of the substance at the plurality of positions in the field of view of the environment, and identify a portion of the captured image having the substance based on the detection map.

In various embodiments of the system, the field of view coincides with the image captured by the image capturing device, and the controller is further configured to map the detection map to the captured image.

In various embodiments of the system, the at least one mirror includes a first mirror and a second mirror. In various embodiments of the system, the first mirror is configured to rotate about an x-axis and the second mirror is configured to rotate about a y-axis.

In various embodiments of the system, the image captured by the image capture device is captured in synchrony with the generating of the detection map.

In various embodiments of the system, identifying a portion of the captured image having the substance based on the detection map includes overlaying the detection map over the captured image of the environment. In various embodiments of the system, overlaying the detection map over the captured image of the environment includes mapping coordinate positions of the detection map to coordinate positions of the captured image.

In various embodiments of the system, the system includes a second light source operably coupled to the controller, where the controller is configured to control the second light source and emit a visible alert light beam toward a region of the environment having a detected presence of the substance.

In various embodiments of the system, the substance includes at least one of gunpowder residue or explosives residue.

In various embodiments of the system, the substance is vape residue, the constituent of the substance includes at least one of propylene glycol or vegetable glycerin, and the predetermined wavelength is absorbable by at least one of the propylene glycol or the vegetable glycerin.

In various embodiments of the system, determining that the constituent of the substance is present includes determining, based on the characteristics of the detected light, that a level of concentration of the constituent of the substance is above a predetermined threshold.

In accordance with aspects of the present disclosure, a method of detecting a substance includes, for each position of a plurality of positions in a field of view of an environment: emitting from a light source a light beam including a predetermined wavelength that is absorbable by a constituent of the substance, controlling at least one mirror to direct the emitted light beam to the position in the field of view, detecting by a detector light resulting from the emitted light beam, and determining whether the constituent of the substance is present at the position in the field of view based on characteristics of the detected light; generating a detection map indicating a presence or an absence of the substance at the plurality of positions in the field of view of the environment; capturing, by an image capture device, an image of the environment; and identifying a portion of the captured image having the substance based on the detection map.

In various embodiments of the method, the field of view coincides with the image captured by the image capturing device, and the method includes mapping the detection map to the captured image.

In various embodiments of the method, the image captured by the image capture device is captured in synchrony with the generating of the detection map.

In various embodiments of the method, identifying a portion of the captured image having the substance based on the detection map includes overlaying the detection map over the captured image of the environment. In various embodiments of the method, overlaying the detection map over the captured image of the environment includes mapping coordinate positions of the detection map to coordinate positions of the captured image.

In various embodiments of the method, the method includes emitting, from a visible light source, a visible alert light beam toward a region of the environment having a detected presence of the substance.

In various embodiments of the method, the substance includes at least one of gunpowder residue or explosives residue.

In various embodiments of the method, the substance is vape residue, the constituent of the substance includes at least propylene glycol or vegetable glycerin, and the predetermined wavelength is absorbable by at least one of the propylene glycol or vegetable glycerin.

In various embodiments of the method, determining that the constituent of the substance is present includes determining, based on the characteristics of the detected light, that a level of concentration of the constituent of the substance is above a predetermined threshold.

BRIEF DESCRIPTION OF DRAWINGS

A better understanding of the features and advantages of the disclosed technology will be obtained by reference to the following detailed description that sets forth illustrative aspects, in which the principles of the technology are utilized, and the accompanying drawings of which.

DETAILED DESCRIPTION

Figure 1:
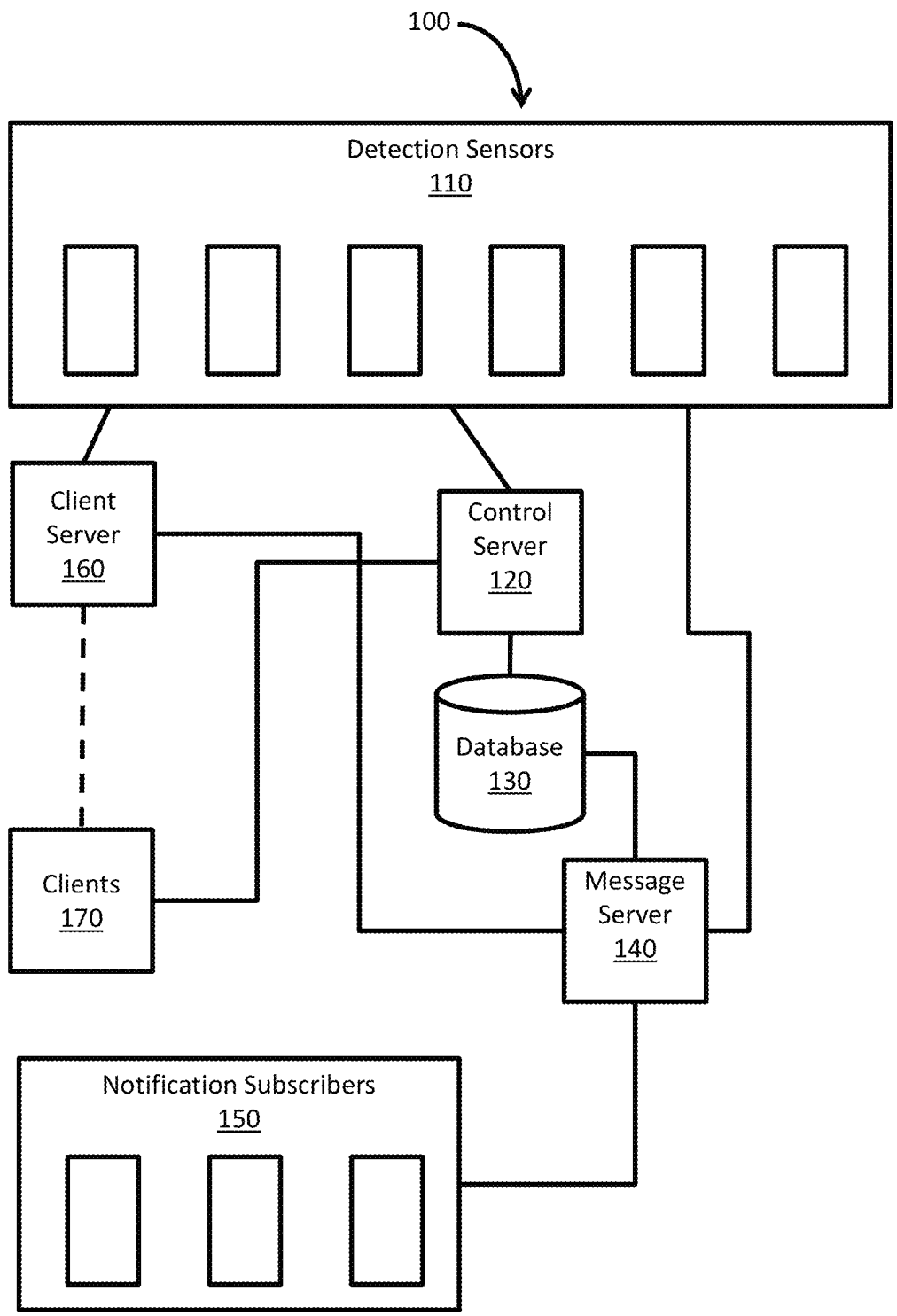
FIG. 1 is a block diagram of an exemplary detection system, provided in accordance with aspects of the present disclosure.

The presently disclosed detection system is described in detail with reference to the drawings, in which like reference numerals designate identical or corresponding elements in each of the several figures.

The present disclosure is generally directed to systems and methods for residue scanning and for mapping residue scanning to video frames. As explained in more detail below, a detection system is configured to scan for the presence of a substance residue and to map the scanned result with a video frame to identify the source of the substance in the video frame. As used herein, the term "residue" includes any constituent of a substance in any amount. When vaping residue, for example, is detected in a scanned grid, the scanned grid can be superimposed onto or mapped to a video frame to identify the person or object that is carrying the vape residue. In this way, persons who vaped do not need to be intercepted at the time or location of the vaping activity and can, instead, be identified at another time or location based on presence of vape residue. Although the present disclosure is applied to detecting vape residue as the primary example, it is intended for the present disclosure to apply to detection of other residues as well, including, without limitation, gunpowder residue, explosives residue, and Anthrax residue, among other substance residues. All such applications are contemplated to be within the scope of the present disclosure. The particular illustrations and aspects disclosed herein are merely exemplary and do not limit the scope or applicability of the disclosed technology.

FIG. 1 illustrates a block diagram of an exemplary detection system 100. The illustrated detection system 100 includes one or more detection sensors 110 which are configured to detect vaping characteristics in the air, a control server 120, and a database 130 storing data. The detection sensors 110 will be described in more detail in connection with FIG. 3. For now, it is sufficient to note that the detection sensors 110 utilize absorption spectroscopy technology to detect the presence of vape residue on persons and objects. As persons skilled in the art will understand, absorption spectroscopy operates using light. As used herein, the term "light" includes visible light as well as non-visible light in the infrared or ultraviolet spectrum. In aspects of the present disclosure, the infrared spectrum is used by the detection sensors 110 to emit and detect light having infrared wavelengths, which persons skilled in the art will recognize. For example, the infrared spectrum can include wavelengths of 0.7 μm-1 mm. The detected data of the detection sensors 110 may be processed by the detection sensors 110 and/or may be processed by the control server 120. Each detection sensor 110 can include circuitry for independently operating itself. The control server 120 may control certain aspects of the detection sensors 110. The control server 120 may communicate with the detection sensors 110 using an application programming interface ("API").

The control server 120 may control the detection sensors 110 collectively, individually, and/or in groups. For example, in the case where several detection sensors 110 may be installed at the same general location, such as several sensors in a single hallway or entranceway, the control server 120 may control such detection sensors 110 collectively. As another example, in the case where several detection sensors 110 are installed at different locations of an environment 10, such as sensors installed in several hallways or entranceways, the control server 120 may control such detection sensors 110 individually or in groups because detection sensors 110 in different locations may experience different conditions.

In accordance with aspects of the present disclosure, the detection sensors 110 may have a learning mode and an active mode. The learning mode may be used to collect data when there is an absence of vape residue and, in that manner, generate baseline data from the detection sensors 110 in the absence of vape residue. The baseline data reflects environmental conditions of the locations where the detection sensors 110 are located, and the use of baseline data can improve accuracy of the vape detection operations. For example, the detection sensors 110 may have internal parameters which can be adjusted based on the baseline data. The detection sensors 110 and/or the control server 120 can set a threshold value for vape residue detection based on the baseline data. The nominal threshold value can be used in the active mode of the detection sensors 110 to detect vaping based on comparing detected data to the threshold value. The detection sensors 110 and/or the control server 120 may enable learning mode at various times of a day to set different thresholds tailored to environmental conditions at different times of a day.

In an aspect of the present disclosure, and as described in more detail below in connection with FIG. 3, vape residue may have a spectroscopy signature, such that vape residue may be detected based on identifying the spectroscopy signature. A detection system 100 may use one or more of baseline data, threshold values, and/or spectroscopy signature to detect vape residue, and any such data or values can be stored in the database 130. The control server 120 may use a query language to communicate with the database 130. The query language may be SQL, MySQL, SSP, C, C++, C#, PHP, SAP, Sybase, Java, JavaScript, or another language which can be used to communicate with a database.

With continuing reference to FIG. 1, the illustrated detection system 100 includes a message server 140, notification subscribers 150, a client server 160, and clients 170. The notification subscribers 150 may be persons who do not have direct access to the control server 120, and the clients 170 may be persons who have direct access to the control server 120. The clients 170 are persons who are responsible for the locations where the detection sensors 110 are installed. For example, the clients 170 may include a principal, vice president, or person in charge at a school, a president at a company, a manager at a hospital or any commercial establishment, or security personnel. This list, however, is exemplary and is not intended to be exhaustive. Other persons having different positions can be included in this list. Communication between the clients 170 and the control server 120 may utilize http, https, ftp, SMTP, or other Internet protocols. The clients 170 may be able to direct the control server 120 to adjust settings for various detection sensors 110. The clients 170 may log-in to the control server 120 to view reports or graphical representations of detection results from the detection sensors 110.

The message server 140 sends alerts to the notification subscribers 150 via a text message, email, instant message, telephone call, audible warning, and/or another type of electronic communication. The notification subscribers 150 may receive the alerts via a computer, smart device, mobile phone, personal digital assistant, tablet, and/or another type of electronic device. The contact information for the notification subscribers 150 can be stored in the database 130, and the message server 140 can access such contact information from the database 130. The client server 160 may communicate with the message server 140 to instruct the message server 140 to notify the notification subscribers 150. The detection sensors 110 can directly instruct the message server 140 to notify the notification subscribers 150. The control server 120 may instruct the message server 140 to notify the notification subscribers 150. Other variations are contemplated to be within the scope of the present disclosure.

Where the detection sensors 110 are configured to detect vape residue, the detection sensors 110 may send an alert to the client server 160 using Internet protocols. The client server 160 can communicate a text message, an email, and/or an app notification to the clients 170 associated with the location where the vaping was detected. In FIG. 1, the connection between the client server 160 and the clients 170 is shown as a dotted line to indicate that communications depend on client connectivity such that communications may not timely reach the clients 170 if the clients 170 have poor telecommunication connectivity. The client server 160 can provide an interface, such as an app interface or a web page interface, for registering and updating information for the clients 170, such as contact information and associations of particular clients with particular locations.

In an aspect of the present disclosure, the database 130 can include historical data, such as data indicating time and location of vape residue detections. The control server 120 may analyze the historical data to predict future occurrences of vaping at particular locations and times, so that appropriate or precautionary measures may be taken. The control server 120 may analyze the historical data stored at the database 130 to identify trends, such as a decreasing or increasing pattern of occurrences of detected vaping.

Figure 2:
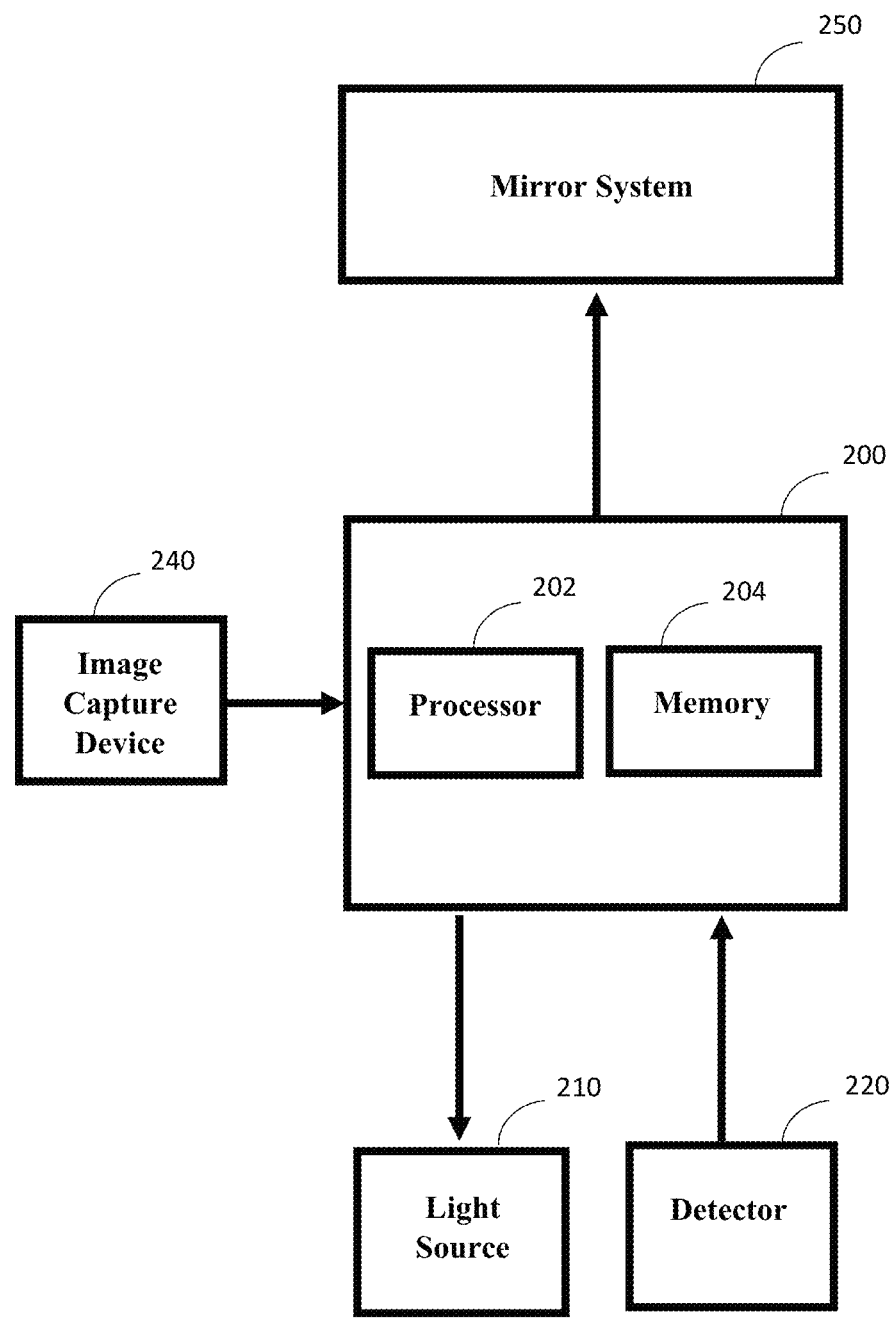
FIG. 2 is a block diagram of an exemplary detection sensor, in accordance with aspects of the present disclosure.
Figure 3:
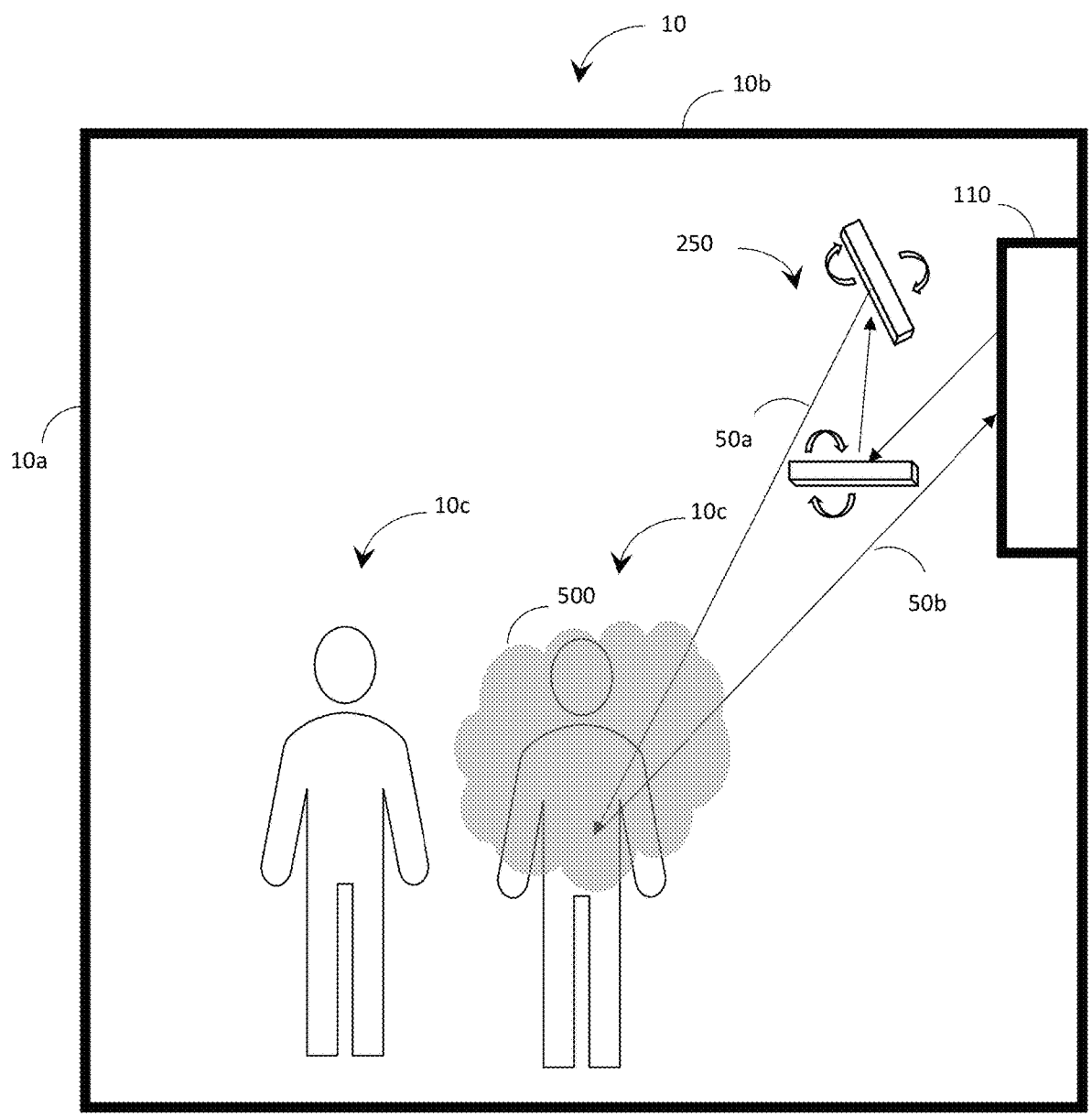
FIG. 3 is a diagram of an exemplary detection environment utilizing detection sensor, in accordance with aspects of the present disclosure.

Referring now to FIGS. 2 and 3, an exemplary detection sensor is provided in accordance with aspects of the present disclosure. The detection sensor includes a controller 200, a light source 210, a detector 220, a temperature control (not shown), an image capture device 240, and a mirror system 250. The detection sensor 110 is described herein as a vape residue detector for detecting the presence of vape residue, but other applications are also contemplated, such as detecting the presence of gunpowder residue, explosives residue, anthrax residue, or other substance residue of interest. The light source 210, detector 220, and the temperature control may be integrated with another device/equipment or can be a stand-alone device.

Figure 4:
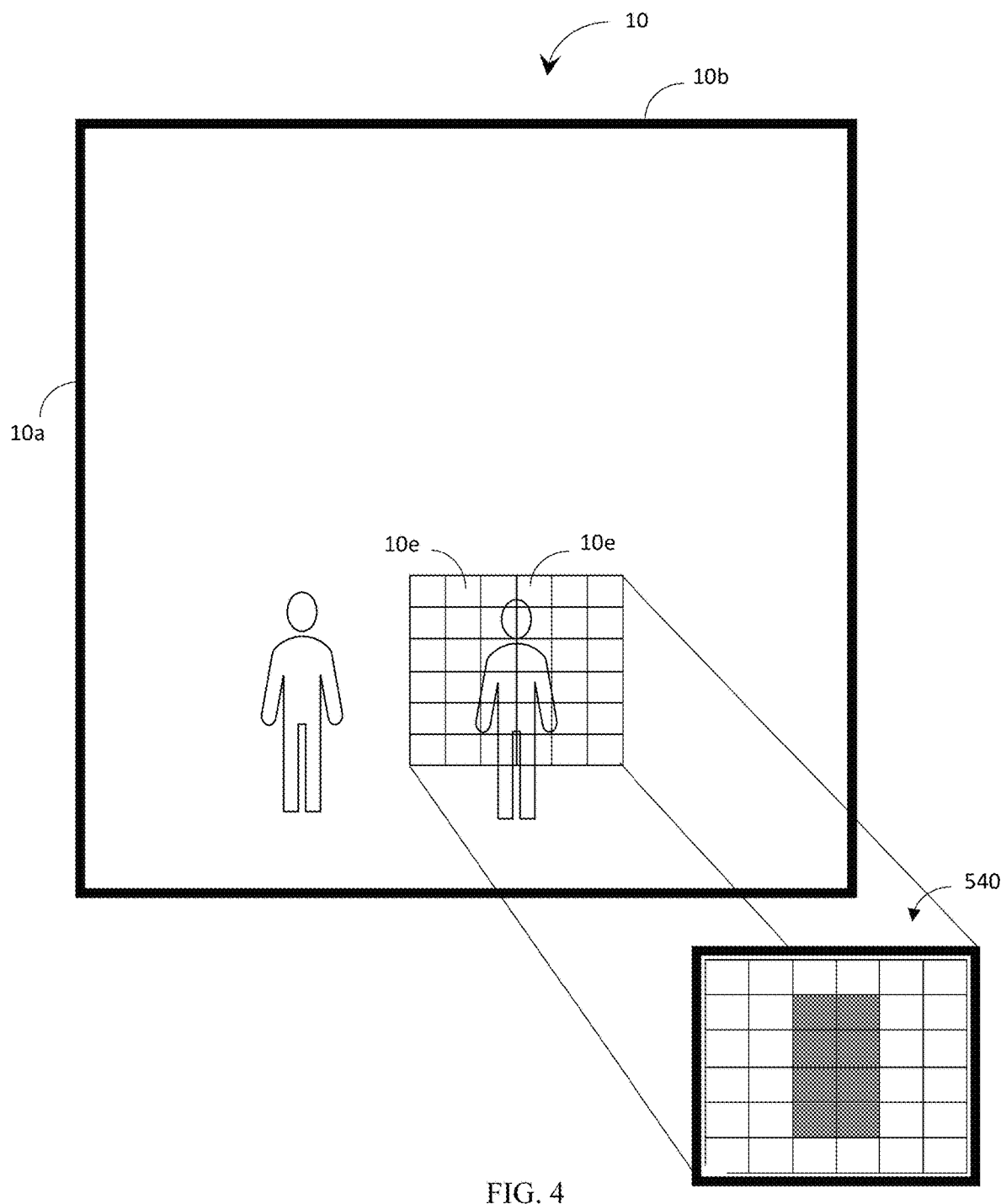
FIG. 4 is an exemplary detection map based on the presence of the substance in the detection environment utilizing detection sensor, in accordance with aspects of the present disclosure.

The controller 200 includes a processor 202 and a memory 204. The processor 202 can be any programmable device that executes machine instructions, such as one or more of a central processing unit, microcontroller, digital signal processor, image processing graphics processing unit, field programmable gate array, and/or programmable logic device, among others. The memory 204 can include volatile memory, such as random-access memory, and/or non-volatile memory, such as flash memory and/or magnetic storage. The memory 204 stores information relating to constituents of vape residue and/or the respective wavelengths that are absorbed by the constituents of vape residue. The memory 204 also stores machine/software instructions which can be executed by the processor 202. The processor 202 executes the machine/software instructions to carry out the processing and computations, which will be described in more detail later herein. The controller 200 is configured to control the light source 210, the detector 220, and the mirror system 250 to scan a field of view for vape residue and to store the scanned field of view in memory 204. The field of view scanned by the light source 210, the detector 220, and the mirror system 250 can be calibrated to coincide with and/or overlap with a field of view of the image capture device 240, which will be described in connection with FIGS. 4-6. In some instances, clients 170 may remotely control the detection sensor 110 to adjust the various field of views.

The light source 210 is communicatively coupled to the controller 200. The light source 210 may be a broadband light source or may include one or more narrow-band light sources, such as a monochromator or tunable laser for precise wavelength control. The narrow-band light source(s) may be designed to enable absorption spectroscopy directed to particular wavelengths or wavelength regions. The narrow-band light source(s) can be configured to emit one or more wavelengths in a controlled manner. Absorption spectroscopy is the investigation and measurement of absorption of radiation, as a function of frequency or wavelength, due to its interaction with a sample, such as investigation and measurement of different materials absorbing energy differently across the electromagnetic spectrum. The amount of absorption at one or more wavelengths is based on the concentration of particular materials, e.g., the number of particles of a constituent of vape residue. As persons skilled in the art will understand, traditional absorption spectroscopy uses wavelength modulation or similar modulation techniques to shift the emitted light wavelength in and out of the targeted wavelength. When emitted light with such modulation passes through a distance without interacting the targeted substance to be detected, the return light intensity would be reduced but would have the same modulation characteristics as the light emitted by the light source. For example, suppose the wavelength of the emitted light is modulated in the form of a sine wave. If the emitted light does not interact with the targeted substance, the return light will also have wavelength modulation in the form of a sine wave. But if the emitted light does interact with the targeted substance, the return light will be distorted and will no longer have wavelength modulation in the form of a sine wave. Rather, the distorted return light will have wavelength modulation with multiple harmonics. Traditional absorption spectroscopy systems can correlate the harmonics amplitudes to the concentration levels of the substance to be detected.

With continuing reference to FIG. 2, the light source 210 is configured to emit one or more laser beams at one or more predetermined wavelengths. The predetermined wavelength(s) may be any wavelength that is absorbed to some degree by the constituents of vape residue, such as, for example, by propylene glycol, vegetable glycerin, nicotine, vitamin E acetate, and/or ingredients used for flavoring vape liquids. In various embodiments, the detection system may include two or more light sources that cooperate to emit light. The light source(s) 210 may be configured to emit multiple light beam(s) targeted to some or all constituents of vape residue. Aspects of the light source 210 and the controller 200 for implementing absorption spectroscopy will be understood by persons skilled in the art. For example, the controller 200 and/or the light source 210 may modulate the wavelength of the emitted light in and out of predetermined wavelengths, in the form of a sine wave. The light source 210 may be a tunable laser diode that allows precise wavelength control. The controller 200 may be a digital signal processor that handles the computations associated with performing wavelength modulation.

The detector 220 is communicatively coupled to the controller 200. The detector 220 may be a photodetector. Aspects of the detector 220 and the controller 200 for implementing absorption spectroscopy will be understood by persons skilled in the art. For example, in various embodiments, the detector 220 is configured to sense light/electromagnetic radiation and to determine changes in the modulation of the light beam emitted from the light source 210. As explained above, changes in the modulation of the light beam emitted from the light source 210 occur when the emitted light interacts with the targeted substance and the modulation characteristics of the emitted light are distorted. When the light emitted from the light source 210 does not interact with the targeted substance, the modulation characteristics of the light are maintained. The return light is demodulated to obtain harmonic amplitudes, if any, which correlate with the concentration level of the targeted substance. The concentration level of the targeted substance is proportionally related to the absorbance of the emitted light by the targeted substance. A higher concentration corresponds with a higher absorption. The controller 200 may be a digital signal processor that handles the computations associated with performing demodulation of the received light.

In order to use harmonics to detect a target substance, the light source 210 should emit light that does not include such harmonics. Therefore, the light source 210 may include high-order active filter circuits that filter out harmonics from the emitted light. Additionally, in order to maintain measurement accuracy, traditional absorption spectroscopy systems include precise temperature control. Because temperature changes vary the wavelength of light emitted by the light source 210, even a slight change in temperature affects measurement readings. As such, the detection system can include a heater and cooler to control temperature. The controller 200 can identify a change in the temperature of the detection sensor 110 that may affect the wavelength and/or modulation characteristics of the emitted light. The temperature control can be operatively coupled to a built-in heater or cooler is configured to heat up or cool down the detection sensor 110 to return the detection sensor 110 to a target temperature. The detection sensor 110 may further include laser modules and/or other components for accurately measuring harmonics based on the returned modulated wavelength. The data provided by the detector 220 may be used by the controller 200 to determine various measures relating to the environment of the detection sensor, such as transmittance, particle concentration, and absorbance. The detection sensor may include two or more detectors(s) 220 that cooperate to measure various light wavelengths. The detection sensor may include a detector 220 configured to measure multiple wavelengths.

The mirror system 250 is operatively coupled to the controller 200. The mirror system 250 includes a mirror and a drive motor operatively coupled to the mirror. In aspects, with reference also to FIG. 3, the mirror of the mirror system 250 may be one or more mirrors, e.g., a first mirror oriented in an x-axis and configured to rotate along the x-axis and a second mirror oriented in a y-axis and configured to rotate along the y-axis. In order to cover a field of view in the environment 10, the light source 210 emits the light beam into the mirror(s) of the mirror system 250 and the controller 200 adjusts the drive motor(s) of the mirror(s) to direct the emitted light beam 50a to a position in the environment 10 in accordance with a grid. As explained in more detailed below, the field of view of the residue detector can be defined as and includes the portions of the environment 10 to which the emitted light beams are directed based on the grid.

The image capture device 240 is communicatively coupled to the controller 200. The image capture device 240 is configured to capture an image of the environment 10. As mentioned above, the captured image 520 of the environment 10 has a field of view that coincides with or overlaps with the field of view of the residue detector, such that the two fields of view can be superimposed onto or mapped to each other.

Referring again to FIG. 1, a detection sensor (110, FIG. 1) can include components which are not specifically illustrated, such as a network interface device which enables communication with other devices wirelessly or via a wired connection. A wireless connection may utilize a wide area network (WAN), local area network (LAN), personal area network (PAN), ad hoc network, and/or cellular network, among other networks. A wired connection may utilize category 5 cable Ethernet (CAT5), CAT5E cable, category 6 Ethernet cable (CAT6), or other network cables.

The detection sensor 110 may include batteries to power the detection sensor 110, such as AA, AAA, or other suitable batteries. The detection sensor 110 may include a connection to a power outlet to receive power from a power grid. The detection sensor 110 may receive power supplied through a network cable based on standards such as, without limitation, Power-over-Ethernet (PoE), PoE+, or 4PPoE.

With continued reference to FIGS. 2 and 3, there is shown a diagram of utilizing an exemplary detection sensor 110 which may be placed in the environment 10, such as an enclosed area. The detection sensor 110, including the detector 220, is placed in the environment 10. The light source 210 of the detection sensor 110 emits a light beam 50a that includes one or more predetermined wavelengths which are absorbable by constituents of vape residue. The emitted modulated light beam 50a is directed by the mirror system 250 based on a grid 540 to positions within the environment 10. The emitted light beam 50a is reflected and/or scattered off various surfaces, e.g., walls 10a, ceilings 10b, and/or people 10c of the environment 10, resulting in reflected and/or scattered light 50b. In the event that vape residue 500 is present, emitted light beam 50a or reflected/scattered light 50b may interact the vape residue 500 and maybe be partially absorbed by the vape residue 500. The detector 220 of the detection sensor 110 receives at least a portion of the reflected/scattered light 50b and determines whether the received light 50b is distorted, as described above. Based on the harmonic amplitude(s), the detection sensor 110 determines the concentration level of the targeted substance. If the concentration level of the targeted substance is above a threshold, the detector 220 indicates the presence of vape residue 500 at the specific position (e.g., position 10e) within the field of view of the residue detector. As the emitted light beam 50a is directed by the mirror system 250 to each position of the residue detector's field of view within the environment 10, the controller 200 generates a detection grid/map 540 that corresponds to the field of view of the residue detector in the environment 10.

Figure 5B:
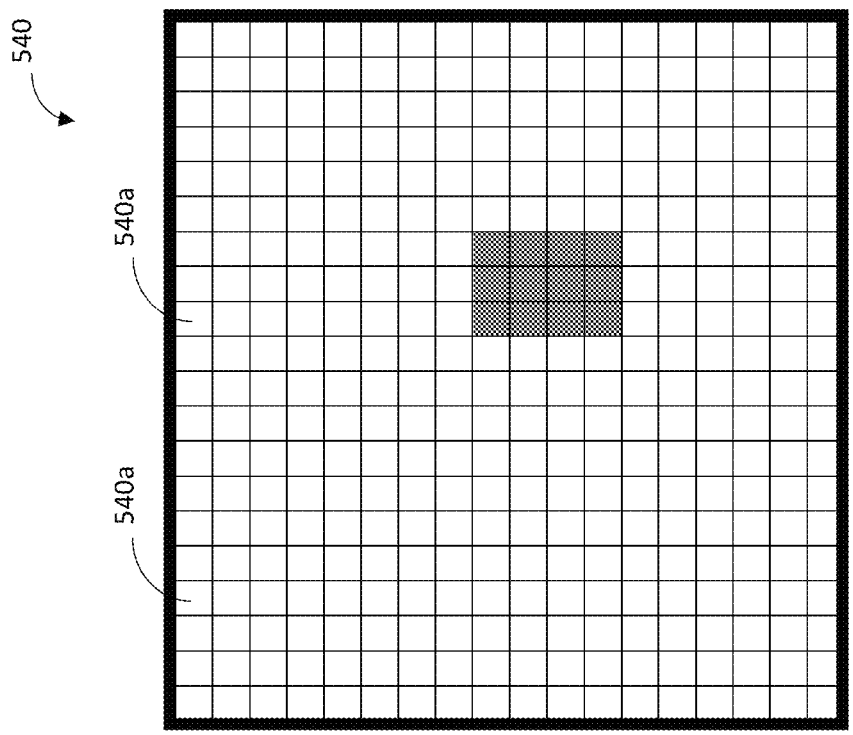
FIG. 5B is an exemplary image of the detection map, in accordance with aspects of the present disclosure.
Figure 5A:
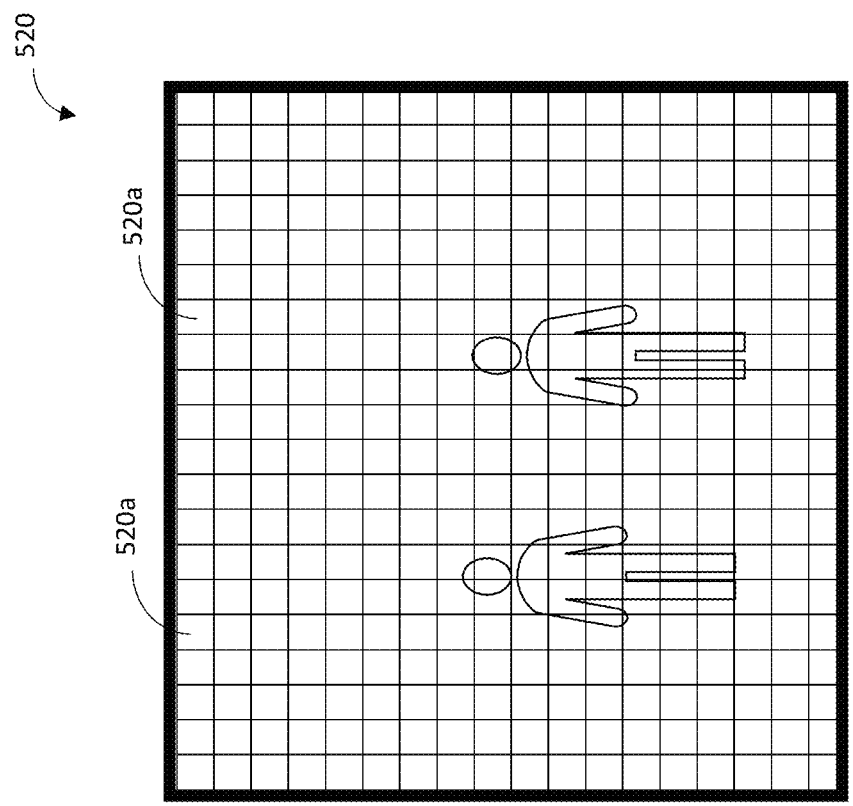
FIG. 5A is an exemplary image of the detection environment, in accordance with aspects of the present disclosure.
Figure 6:
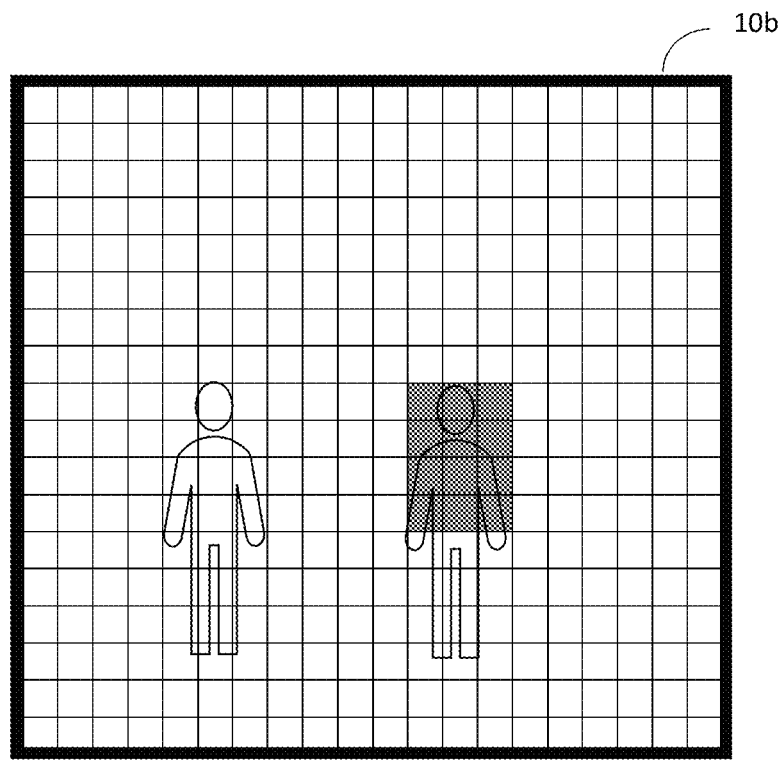
FIG. 6 is an exemplary display of the detection map over the image of the detection environment, in accordance with aspects of the present disclosure.

When the emitted light beam 50a has reached each coordinate position 10e of the environment 10, the detection map 540 is generated and indicates all coordinate positions that contain the presence of vape smoke/vapor 500. With reference to FIG. 5, the residue detection map 540 is overlaid over the captured image 520 captured by the image capture device (240, FIG. 2). The captured image 520 can be captured in synchrony with the generation of the residue detection map 540. For example, the captured image 520 can be captured at the time the residue detection map 540 is generated. As explained above, the field of view of the captured image 520 coincides with and/or overlaps with the field of view of the residue detector, such that the detection map 540 can be superimposed or mapped to the captured image 520 by mapping the image coordinate positions 520a to the detection coordinate positions 540a. An example of the mapping/superposition is shown in FIG. 6. The detection system 100 can trigger an alert when the detection map 540 indicates presence of vape residue, for example, and the alert may send the superimposed image to notification subscribers 150 or to clients 170, as shown in FIGS. 1 and 6, via text message, email, instant message, telephone call, audible warning, or other types of electronic communication capable of viewing the resulting image. The superimposed image can be used to identify the portion of the captured image corresponding to the detected vape residue. Additionally, and/or alternatively, the detection system 100 may further include an alert light beam that emits one or more light beams directed at the positions in the environment 10 corresponding to the detected vape residue, which visually alerts monitoring personnel of the detected residue in real time.

Figure 7:
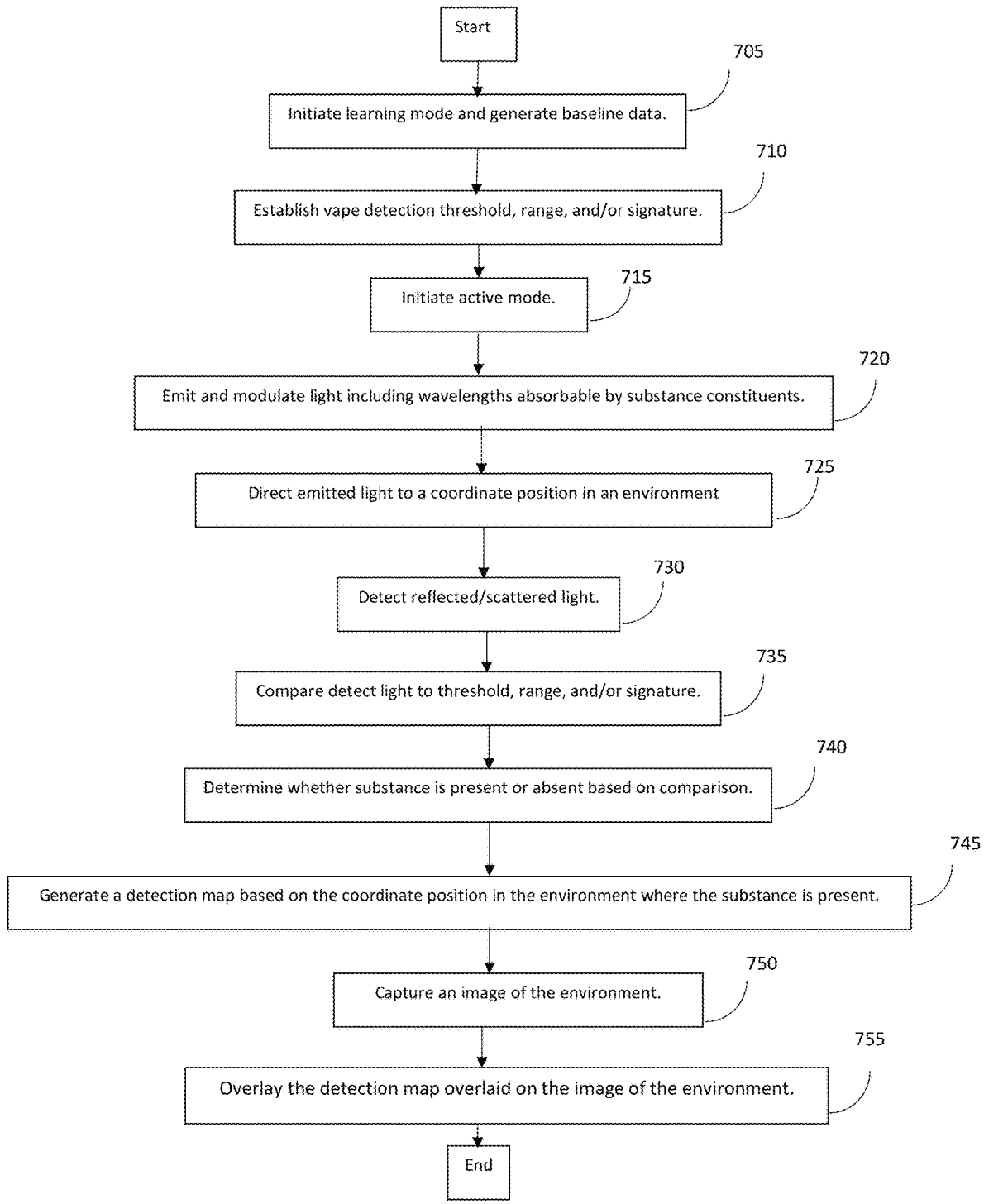
FIG. 7 is a flow diagram of an exemplary operation of detecting a substance, in accordance with aspects of the present disclosure.

Referring now to FIG. 7, there is shown an exemplary detection operation. At block 705, the operation initiates learning mode and generates baseline data. At block 710, the operation establishes one or more vape detection thresholds, ranges, and/or signatures, based on the baseline data. At block 715, active detection of vape residue is initiated. At block 720, the operation emits and modulates light from a light source that includes a predetermined wavelength which is absorbable by one or more constituents of vape residue. At block 725, the operation directs the emitted light to a position in an environment. As described above, the emitted light is directed to a position in the environment within a field of view of the residue detector. At block 730, the operation detects and demodulates at least a portion of the reflected/scattered light. The detected light is demodulated and the harmonic amplitudes are obtained to determine a level of concentration of the constituents of vape At block 735, the operation compares the concentration level to one or more thresholds and/or ranges. At block 740, the operation determines whether vape is present or absent based on the comparison between the level of concentration of the constituents of vape residue and the thresholds. At block 745, the operation generates a detection map of each coordinate position in the field of review of the residue detector and indicates the coordinate positions where the residue constituent was present. At block 750, the operation captures an image of the environment. As described above, the field of view of the captured image coincides with and/or overlaps with the field of view of the residue detector. At block 755, the operation overlays the detection map over the captured image to identify the persons or objects which triggered the vape residue detection. The operation of FIG. 7 is exemplary, and variations are contemplated to be within the scope of the present disclosure. For example, in various aspects, the operation may not include a learning mode and may not include blocks 705, 710. Rather, thresholds, ranges, and/or signatures may be predetermined, such that the operation begins in active mode. In various aspects, after the learning mode of blocks 705, 710 are performed, the active mode blocks 715-755 can be repeated without performing learning mode again for some time. In various aspects, various blocks of the illustrated operation may be performed by different devices. For example, blocks 720-730 may be performed by a detection sensor and blocks 735-755 may be performed by a control server. In various aspects, the entire operation of FIG. 7 can be performed by a detection sensor. Other variations are contemplated to be within the scope of the present disclosure.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

What is claimed is:

1. A detection system, comprising:
    a light source configured to emit a light beam, the light beam including a predetermined wavelength that is absorbable by a constituent of a substance;
    a detector configured to detect light resulting from the emitted light beam;
    at least one mirror including a drive motor;
    an image capturing device configured to capture an image of an environment; and
    a controller in communication with the light source, the at least one mirror, and the detector, the controller configured to calibrate the drive motor of the at least one mirror to a plurality of positions which coincide with a field of view of the image capturing device, the controller further configured to, for each position of the plurality of positions coinciding with the field of view of the image capturing device:
        control the light source to emit the light beam,
        control the at least one mirror to the respective position to direct the emitted light beam to a coincident portion of the field of view,
        control the detector to detect light resulting from the emitted light beam, and
        determine whether the constituent of the substance is present for the respective position of the at least one mirror based on characteristics of the detected light,
    wherein the controller is further configured to generate a detection map indicating a presence or an absence of the substance at the plurality of positions, and identify a portion of the captured image having the substance based on the detection map and based on the coincidence of the plurality of positions with the field of view of the image capturing device.

2. The detection system according to claim 1, wherein the controller is further configured to map the detection map to the captured image based on the coincidence of the plurality of positions with the field of view of the image capturing device.

3. The detection system according to claim 2, wherein the at least one mirror includes a first mirror and a second mirror.

4. The detection system according to claim 3, wherein the first mirror is configured to rotate about an x-axis and the second mirror is configured to rotate about a y-axis.

5. The detection system according to claim 1, wherein the image captured by the image capture device is captured in synchrony with the generating of the detection map.

6. The detection system according to claim 5, wherein identifying a portion of the captured image having the substance based on the detection map includes overlaying the detection map over the captured image of the environment.

7. The detection system according to claim 6, wherein in overlaying the detection map over the captured image of the environment includes mapping coordinate positions of the detection map to coordinate positions of the captured image.

8. The detection system according to claim 1, further comprising:
    a second light source operably coupled to the controller, the controller configured to control the second light source and emit a visible alert light beam toward a region of the environment having a detected presence of the substance.

9. The detections system according to claim 1, wherein the substance includes at least one of gunpowder residue or explosives residue.

10. The detection system according to claim 1, wherein the substance is vape residue,
    wherein the constituent of the substance includes at least one of propylene glycol or vegetable glycerin, and
    wherein the predetermined wavelength is absorbable by at least one of the propylene glycol or the vegetable glycerin.

11. The detection system according to claim 1, wherein determining that the constituent of the substance is present includes determining, based on the characteristics of the detected light, that a level of concentration of the constituent of the substance is above a predetermined threshold.

12. A method of detecting a substance, the method comprising:
    calibrating a drive motor of at least one mirror to a plurality of positions which coincide with a field of view of an image capture device;
    for each position of the plurality of positions coinciding with the field of view of an image capturing device:
        emitting, from a light source, a light beam including a predetermined wavelength that is absorbable by a constituent of the substance,
        controlling the at least one mirror to the respective position to direct the emitted light beam to a coincident portion of the field of view,
        detecting, by a detector, light resulting from the emitted light beam, and
        determining whether the constituent of the substance is present for the respective position of the at least one mirror based on characteristics of the detected light;
    generating a detection map indicating a presence or an absence of the substance at the plurality of positions;
    capturing, by the image capture device, an image of the environment; and
    identifying a portion of the captured image having the substance based on the detection map and based on the coincidence of the plurality of positions with the field of view of the image capturing device.

13. The method according to claim 12, further comprising mapping the detection map to the captured image based on the coincidence of the plurality of positions with the field of view of the image capturing device.

14. The method according to claim 12, wherein the image captured by the image capture device is captured in synchrony with the generating of the detection map.

15. The method according to claim 14, wherein identifying a portion of the captured image having the substance based on the detection map includes overlaying the detection map over the captured image of the environment.

16. The method according to claim 15, wherein overlaying the detection map over the captured image of the environment includes mapping coordinate positions of the detection map to coordinate positions of the captured image.

17. The method according to claim 12, further comprising:
   emitting, from a visible light source, a visible alert light beam toward a region of the environment having a detected presence of the substance.

18. The method according to claim 12, wherein the substance includes at least one of gunpowder residue or explosives residue.

19. The method according to claim 12, wherein the substance is vape residue,
   wherein the constituent of the substance includes at least propylene glycol or vegetable glycerin, and
   wherein the predetermined wavelength is absorbable by at least one of the propylene glycol or vegetable glycerin.

20. The method according to claim 12, wherein determining that the constituent of the substance is present includes determining, based on the characteristics of the detected light, that a level of concentration of the constituent of the substance is above a predetermined threshold.

* * * * *